(12) United States Patent
Betts et al.

(10) Patent No.: US 11,274,344 B2
(45) Date of Patent: Mar. 15, 2022

(54) ENHANCED LIGATION IN SEQUENCING LIBRARY PREPARATION

(71) Applicant: GRAIL, Inc., Menlo Park, CA (US)

(72) Inventors: Craig Betts, San Jose, CA (US); Byoungsok Jung, Atherton, CA (US)

(73) Assignee: GRAIL, Inc., Menlo Park, CA (US)

( * ) Notice: Subject to any disclaimer, the term of this patent is extended or adjusted under 35 U.S.C. 154(b) by 0 days.

(21) Appl. No.: 15/942,214

(22) Filed: Mar. 30, 2018

(65) Prior Publication Data

US 2018/0291445 A1   Oct. 11, 2018

Related U.S. Application Data

(60) Provisional application No. 62/479,001, filed on Mar. 30, 2017.

(51) Int. Cl.
| | | |
|---|---|---|
| *C12Q 1/6874* | (2018.01) | |
| *C12N 15/10* | (2006.01) | |
| *C12Q 1/6806* | (2018.01) | |
| *C12N 15/66* | (2006.01) | |
| *C12Q 1/6869* | (2018.01) | |

(52) U.S. Cl.
CPC ....... *C12Q 1/6874* (2013.01); *C12N 15/1093* (2013.01); *C12N 15/66* (2013.01); *C12Q 1/6806* (2013.01); *C12Q 1/6869* (2013.01)

(58) Field of Classification Search
CPC .. C12Q 1/6874; C12Q 1/6806; C12Q 1/6869; C12N 15/1093; C12N 15/66
See application file for complete search history.

(56) References Cited

U.S. PATENT DOCUMENTS

| | | | |
|---|---|---|---|
| 4,683,195 | A | 7/1987 | Mullis et al. |
| 6,818,395 | B1 | 11/2004 | Quake et al. |
| 7,169,560 | B2 | 1/2007 | Lapidus et al. |
| 7,282,337 | B1 | 10/2007 | Harris et al. |
| 7,297,518 | B2 | 11/2007 | Quake et al. |
| 7,666,593 | B2 | 2/2010 | Lapidus |
| 7,897,345 | B2 | 3/2011 | Lapidus et al. |
| 7,984,015 | B2 | 5/2011 | Rothberg et al. |
| 8,262,900 | B2 | 9/2012 | Rothberg et al. |
| 8,306,757 | B2 | 11/2012 | Rothberg et al. |

(Continued)

FOREIGN PATENT DOCUMENTS

| | | |
|---|---|---|
| WO | 99/04041 | 1/1999 |
| WO | 2007/052006 | 5/2007 |

(Continued)

OTHER PUBLICATIONS

Levin et al. (Nucleic Acids Research, 2006, vol. 34, No. 20 e142, 11 pages).*

(Continued)

*Primary Examiner* — Robert H Havlin
(74) *Attorney, Agent, or Firm* — Benjamin C. Pelletier; Haynes and Boone LLP (57) ABSTRACT

Methods for preparing a sequencing library from a DNA-containing test sample are provided. In some embodiments, the methods involve rescuing a partially ligated DNA fragment to enhance library preparation conversion efficiencies. In some embodiments, the methods involve improving recovery of duplex sequence information from double-stranded DNA.

15 Claims, 4 Drawing Sheets

(56) References Cited

U.S. PATENT DOCUMENTS

| | | | |
|---|---|---|---|
| 8,349,167 B2 | 1/2013 | Rothberg et al. | |
| 8,426,898 B2 | 1/2013 | Rothberg et al. | |
| 8,546,128 B2 | 10/2013 | Schultz et al. | |
| 8,574,835 B2 | 11/2013 | Hinz et al. | |
| 8,673,627 B2 | 3/2014 | Nobile et al. | |
| 2002/0164629 A1 | 11/2002 | Quake et al. | |
| 2009/0026082 A1 | 1/2009 | Rothberg et al. | |
| 2009/0127589 A1 | 5/2009 | Rothberg et al. | |
| 2009/0156412 A1 | 6/2009 | Harris et al. | |
| 2009/0191565 A1 | 7/2009 | Lapidus et al. | |
| 2010/0035252 A1 | 2/2010 | Rothberg et al. | |
| 2010/0137143 A1 | 6/2010 | Rothberg et al. | |
| 2010/0167954 A1* | 7/2010 | Earnshaw | C12Q 1/6806 506/17 |
| 2010/0188073 A1 | 7/2010 | Rothberg et al. | |
| 2010/0197507 A1 | 8/2010 | Rothberg et al. | |
| 2010/0282617 A1 | 11/2010 | Rothberg et al. | |
| 2010/0300559 A1 | 12/2010 | Schultz et al. | |
| 2010/0300895 A1 | 12/2010 | Noble et al. | |
| 2010/0301398 A1 | 12/2010 | Rothberg et al. | |
| 2010/0304982 A1 | 12/2010 | Hinz et al. | |
| 2013/0116130 A1 | 5/2013 | Fu et al. | |
| 2015/0197798 A1 | 7/2015 | Xu et al. | |
| 2015/0299767 A1 | 10/2015 | Armour et al. | |
| 2015/0376608 A1 | 12/2015 | Kaper et al. | |
| 2016/0017412 A1 | 1/2016 | Srinivasan et al. | |
| 2016/0304947 A1* | 10/2016 | Hajeri | C12Q 1/6837 |
| 2016/0319345 A1 | 11/2016 | Gnerre et al. | |
| 2016/0333416 A1 | 11/2016 | Babiarz et al. | |
| 2017/0016048 A1 | 1/2017 | Blauwkamp et al. | |
| 2017/0044525 A1 | 2/2017 | Kaper et al. | |
| 2017/0327882 A1 | 11/2017 | Betts et al. | |

FOREIGN PATENT DOCUMENTS

| | | | |
|---|---|---|---|
| WO | 2009/072972 | 6/2009 | |
| WO | 2009/109753 | 9/2009 | |
| WO | 2009/133466 | 11/2009 | |
| WO | 2013/142389 | 9/2013 | |
| WO | 2014/008447 | 1/2014 | |
| WO | 2014/066179 | 5/2014 | |
| WO | 2015/057319 | 4/2015 | |
| WO | 2015/094861 | 6/2015 | |
| WO | 2015/117040 | 8/2015 | |
| WO | 2015/122967 | 8/2015 | |
| WO | WO2015134552 | * 9/2015 | C12P 19/34 |
| WO | 2015/168161 | 11/2015 | |
| WO | 2015/200609 | 12/2015 | |
| WO | 2016/034433 | 3/2016 | |
| WO | 2016/170147 | 10/2016 | |
| WO | 2016/172373 | 10/2016 | |
| WO | 2016/176091 | 11/2016 | |
| WO | 2017/040306 | 3/2017 | |
| WO | 2017/044574 | 3/2017 | |
| WO | 2017/218512 | 12/2017 | |
| WO | 2018/031929 | 2/2018 | |

OTHER PUBLICATIONS

Latorra et al. (Molecular and Cellular Probes 17 (2003) 253-259).*
Rahman et al. (Nucleosides, Nucleotides, and Nucleic Acids, 26:1625-1628, 2007).*
"International Search Report and Written Opinion," PCT Application No. PCT/US2017/068196, dated Mar. 2, 2018.
"International Search Report and Written Opinion," PCT Application No. PCT/US2018/025475, dated Aug. 10, 2018.
Bettegowda et al., "Detection of circulating tumor DNA in early- and late-stage human malignancies," (2014) SciTrans Med 6(224):1-11.
Braslavsky et al., "Sequence information can be obtained from single DNA molecules," (2003) PNAS 100(7):3960-64.
Cheng et al., "Memorial Sloan Kettering—Integrated Mutation Profiling of Actionable Cancer Targets (MSK-IMPACT)," (2015) Journal of Molecular Diagnostics, 17(3):251-64.
Duncavage et al., "Hybrid Capture and Next-Generation Sequencing Identify Viral Integration Sites from Formalin-Fixed, Paraffin-Embedded Tissue," (2011) J Mol Diagn. 13(3):25-333.
Harris et al., "Single-Molecule DNA Sequencing of a Viral Genome," (2008) Science, 320:106-9.
Head et al., "Library construction for next-generation sequencing: Overviews and challenges" (2014) BioTechniques 61.
Jiang et al., "Lengthening and shortening of plasma DNA in hepatocellular carcinoma patients," (2015) PNAS 112(11):E1317-E1325.
Johannsen et al., "Enzymatic polymerisation involving 2-amino-LNA nucleotides," (2012) Bioorganic & Medicinal Chemistry Letters, 22(10):3522-26.
Kennedy et al., "Detecting ultralow-frequency mutations by Duplex Sequencing." Nature (2014) Protocols 9(11):2586-606.
Kuwahara et al., "Study on Suitability of KOD DNA Polymerase for Enzymatic Production of Artificial Nucleic Acids Using Base/Sugar Modified Nucleoside Triphosphates," (2010) Molecules, 15(11):8229-40.
Marguiles et al., "Genome sequencing in microfabricated high-density picolitre reactors," (2005) Nature 437(7057):376-380.
Maxam et al., "A New Method for Sequencing DNA," (1977) PNAS 74(2):560-64.
Moudrianakis et al., "Base Sequencing Determination in Nucleic Acids with the Electron Microscope III," (1965) Chemistry 53(3):564-71.
Mouliere et al., "Circulating tumor-derived DNA is shorter than somatic DNA in plasma" (2015) PNAS 112(11):3178-79.
Mouliere et al., "Multi-marker Analysis of Circulatig Cell-free DNA Toward Personalized Medicine for Colorectal Cancer," (2014) Mol Oncol., 8(5):927-47.
Nagalakshmi et al., "RNA-Seq: A Method for Comprehensive Transcriptome Analysis," (2010) Current Protocols in Molecular Biology.
Newman et al., "An ultrasensitive method for quantitating circulating tumor DNA with broad patient coverage," (2014) Nat Med 20(5):548-54.
Nguyen "Design of modified A*U and G*C base pairs with similar stability, implication for teh DNA sequencing by hybridization," (1997) Tetrahedron Letters 38 (43):7515-18.
Nguyen et al., "Modification of DNA duplexes to smooth their thermal stability independently of their base content for DNA sequencing by hybridization" (1997) NAR 25(15):3059-65.
Nguyen et al., "Smoothing of the thermal stability of DNA dupexes by using modified nucleosides and chaotropic agents," (1999) NAR, 27(6):1492-98.
Nguyen et al. , "Studies towards the design of a modified GC base pair with stability similar to that of the at base pair," (1997) Tetrahedron Letters, 38(23):4082-86.
Nguyen et al., "The stability of duplexes involving AT and/or G4Etc base pairs is not dependent on their AT/G4EtC ratio content. Implication for DNA sequencing by hybridization" (1998) NAR,26(18):4249-58.
Sanger et al., "DNA Sequencing with Chain-terminating Inhibitors," (1977) PNAS 74(12):5463-67.
Soni et al., "Progress toward ultrafast DNA sequencing using solid-state nanopores," (2007) Clin. Chem, 53(11):1996-2001.
Turchinovich et al., "Capture and Amplification by Tailing and Switching (CATS). An ultrasensitive ligation-independent method for deep sequencing from picogram amounts of DNA and RNA," (2014) RNA Biology, Landes Bioscience, 11(7):817-28.
Veedu et al., "In vitro incorporation of LNA nucleotides," (2007) Nucleosides, Nucleotides and Nucleic Acids, 26(8-9):1207-10.
Veedu et al., "Locked nucleic acid nucleoside triphosphates and polymerases: on the way towards evolution of LNA aptamers," (2009) Molecular Biosystems 5(8):787-92.
Veedu et al., "Locked Nucleic Acids: Promising Nucleic Acid Analogs for Therapeutic Applications," (2010) Chemistry & Biodiversity, 7(3):536-42.

(56) References Cited

OTHER PUBLICATIONS

Veedu et al., "Polymerase chain reaction and transcription using locked nucleic acid nucleotide triphosphates," (2008) Journal of the American Chemical Society, 130(26):8124-25.
Veedu et al., "Polymerase directed incorporation studies of LNA-G nucleoside 5'-triphosphate and primer extension involving all four LNA nucleotides," (2010) New Journal of Chemistry, 34(5):877.
Veedu et al., "Polymerase-directed synthesis of C5-ethynyl locked nucleic acids," (2010) Bioorganic & Medicinal Chemistry Letters, 20(22):6565-68.
Bodi et al., "Comparison of Commercially Available Target Enrichment Methods for Next-Generation Sequencing," (2013) J. Biomol Tech. 24(2):73-86.

* cited by examiner

ENHANCED LIGATION IN SEQUENCING LIBRARY PREPARATION

CROSS REFERENCE TO RELATED APPLICATIONS

This application claims priority benefit of the filing date of U.S. Provisional Patent Application Ser. No. 62/479,001, filed on Mar. 30, 2017, the disclosure of which application is herein incorporated by reference in its entirety.

FIELD OF THE INVENTION

The present invention relates to molecular biology techniques and methods for preparing a sequencing library from a DNA-containing test sample.

BACKGROUND OF THE INVENTION

The ligation efficiency of A-tailed fragments is a critical part of some library construction protocols for next generation sequencing. However, the ligation efficiency of double-stranded A-tailed fragments to adapters with 3' T overhangs is relatively inefficient, and represents one of the main limitations of library construction efficiency. There is a need for new methods for increasing ligation efficiency in sequencing library preparation procedures.

SUMMARY OF THE INVENTION

Aspects of the invention involve methods for preparing a sequencing library from a DNA-containing test sample. In some embodiments, the methods involve rescuing a partially-ligated DNA fragment to enhance library preparation conversion efficiencies. In some embodiments, the methods involve improving recovery of duplex sequence information from double-stranded DNA.

In some embodiments, a method for preparing a sequencing library from a test sample comprising a plurality of double-stranded DNA fragments involves: (a) obtaining a test sample comprising a plurality of double-stranded DNA (dsDNA) fragments, wherein the dsDNA fragments each comprise a forward strand and a reverse strand; (b) contacting the test sample with a plurality of dsDNA adapters, wherein the dsDNA adapters comprise one or more modified bases having a melting temperature that is higher than a melting temperature of a non-modified DNA base; (c) ligating the dsDNA adapters to the dsDNA fragments to create a plurality of dsDNA adapter-fragment constructs; and (d) amplifying the dsDNA adapter-fragment constructs to generate a sequencing library.

In some embodiments, a method for detecting cancer, determining cancer stage, monitoring cancer progression, and/or determining a cancer classification in a subject known to have or suspected of having cancer involves: (a) obtaining a test sample comprising a plurality of double-stranded DNA (dsDNA) fragments from the subject, wherein the dsDNA fragments comprise a forward strand and a reverse strand; (b) contacting the test sample with a plurality of dsDNA adapters, wherein the dsDNA adapters comprise one or more modified bases at a 3'-end of a dsDNA adapter, the one or more modified bases having a melting temperature that is higher than a melting temperature of a non-modified DNA base; (c) ligating the double-stranded DNA adapters to the plurality of dsDNA fragments to create a plurality of dsDNA adapter-fragment constructs; (d) preparing a sequencing library by amplifying the plurality of dsDNA adapter-fragment constructs; (e) sequencing the sequencing library to obtain a plurality of sequence reads; and (f) analyzing the plurality of sequence reads to detect the presence or absence of cancer, determine cancer status, monitor cancer progression and/or determine a cancer classification in the subject.

In some embodiments, the dsDNA fragments comprise cell-free DNA (cfDNA) fragments. In some embodiments, a dsDNA fragment is modified prior to ligation of the double-stranded DNA adapters. In some embodiments, the modification comprises end-repairing, A-tailing, phosphorylation, or any combination thereof.

In some embodiments, the test sample comprises whole blood, a blood fraction, plasma, serum, urine, fecal, saliva, a tissue biopsy, pleural fluid, pericardial fluid, cerebral spinal fluid, peritoneal fluid, or any combination thereof. In some embodiments, the test sample is a plasma sample. In some embodiments, the test sample comprises dsDNA fragments originating from healthy cells and from cancer cells. In some embodiments, the dsDNA fragments are isolated from the test sample prior to step (c). In some embodiments, the dsDNA adapters are ligated to a first end and a second end of the dsDNA fragments.

In some embodiments, the dsDNA adapters comprise a fork-shaped sequencing adapter formed by annealing a pair of partially complementary oligonucleotides to one another, wherein the fork-shaped sequencing adapter comprises a first double-stranded region, formed from hybridization between two complementary regions, and a first single-stranded region.

In some embodiments, the one or more modified bases are located at a 3' end of the first double-stranded region of the fork-shaped sequencing adapter. In some embodiments, the one or more modified bases are located upstream of a 3' end of the fork-shaped sequencing adapter. In some embodiments, the one or more modified bases are located upstream of a 5' end of the fork-shaped sequencing adapter.

In some embodiments, the dsDNA adapters are hairpin adapters. In some embodiments, the dsDNA adapters are linear adapters. In some embodiments, the one or more modified bases are selected from the group consisting of: locked nucleic acid (LNA) bases, bridged nucleic acid (BNA) bases, super T (5-hydroxybutynl-2'-deoxyuridine), C-5 propynyl-U, 2'-Omethyl, or any combination thereof. In some embodiments, the ligase is a T4 DNA ligase. In some embodiments, the ligase is a T7 DNA ligase.

In some embodiments, the methods further comprise enriching the sequencing library for one or more target dsDNA fragments that are known to be, or suspected of being, indicative of cancer. In some embodiments, the sequence reads are obtained from a next-generation sequencing (NGS) procedure. In some embodiments, the sequence reads are obtained from massively parallel sequencing using a sequencing-by-synthesis procedure. In some embodiments, the sequence reads are obtained from a paired-end sequencing procedure.

In some embodiments, monitoring cancer progression further comprises monitoring disease progression, monitoring therapy, or monitoring cancer growth. In some embodiments, the cancer classification comprises determining a cancer type and/or a cancer tissue of origin. In some embodiments, the cancer comprises a carcinoma, a sarcoma, a myeloma, a leukemia, a lymphoma, a blastoma, a germ cell tumor, or any combination thereof.

In some embodiments, a method for preparing a sequencing library from a test sample comprising a plurality of double-strand DNA (dsDNA) fragments involves: (a)

obtaining a test sample comprising a plurality of dsDNA fragments, wherein the dsDNA fragments each comprise a forward strand and a reverse strand; (b) providing a reaction mixture comprising one or more modified bases having a melting temperature that is higher than a melting temperature of a non-modified DNA base; (c) adding the one or more modified bases to the dsDNA fragments through a polymerase reaction to create a plurality of modified-dsDNA constructs; and (d) amplifying the modified-dsDNA constructs to generate a sequencing library.

In some embodiments, the dsDNA fragments are cell-free DNA (cfDNA) fragments. In some embodiments, a plurality of dsDNA adapters are ligated to both ends of the dsDNA fragments. In some embodiments, the dsDNA fragments are modified prior to ligation of the dsDNA adapters. In some embodiments, the modification comprises end-repairing and/or phosphorylation of the 5' ends prior to ligation of the dsDNA adapters.

In some embodiments, the test sample comprises whole blood, a blood fraction, plasma, serum, urine, fecal, saliva, a tissue biopsy, pleural fluid, pericardial fluid, cerebral spinal fluid, peritoneal fluid, or any combination thereof. In some embodiments, the test sample is a plasma sample. In some embodiments, the test sample comprises dsDNA originating from healthy cells and from cancer cells.

In some embodiments, the dsDNA adapters comprise a fork-shaped sequencing adapter formed by annealing a pair of partially complementary oligonucleotides to one another, wherein the fork-shaped sequencing adapter comprises a first double-stranded region, formed from hybridization between two complementary regions, and a first single-stranded region. In some embodiments, the fork-shaped adapters further comprise one or more modified bases located at each 3' end of the fork-shaped adapters. In some embodiments, the one or more modified bases are located upstream of the 3' ends. In some embodiments, the one or more modified bases are located upstream of the 5' ends.

In some embodiments, the plurality of dsDNA adapters are hairpin adapters. In some embodiments, the plurality of dsDNA adapters are linear adapters. In some embodiments, the one or more modified bases are selected from the group consisting of: locked nucleic acid (LNA) bases, bridged nucleic acid (BNA) bases, super T (5-hydroxybutynl-2'-deoxyuridine), C-5 propynyl-U, 2'-Omethyl, or any combination thereof.

In some embodiments, the ligase is a T4 DNA ligase. In some embodiments, the ligase is a T7 DNA ligase.

In some embodiments, the methods further comprise sequencing the sequencing library to obtain a plurality of sequence reads, and analyzing the sequence reads to detect a presence or absence of cancer, determine cancer status, monitor cancer progression and/or determine a cancer classification. In some embodiments, the methods further comprise enriching the sequencing library for one or more target dsDNA fragments that are known to be, or suspected of being, indicative of cancer.

In some embodiments, the sequence reads are obtained from a next-generation sequencing (NGS) procedure. In some embodiments, the sequence reads are obtained from massively parallel sequencing using a sequencing-by-synthesis procedure. In some embodiments, the sequence reads are obtained from a paired-end sequencing procedure.

In some embodiments, monitoring cancer progression further comprises monitoring disease progression, monitoring therapy, or monitoring cancer growth. In some embodiments, the cancer classification comprises determining a cancer type and/or a cancer tissue of origin. In some embodiments, the cancer comprises a carcinoma, a sarcoma, a myeloma, a leukemia, a lymphoma, a blastoma, a germ cell tumor, or any combination thereof.

DEFINITIONS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit, unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application, as do the following, each of which is incorporated by reference herein in its entirety: Kornberg and Baker, DNA Replication, Second Edition (W. H. Freeman, N.Y., 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6th edition (Saunders, 2007).

All publications mentioned herein are expressly incorporated herein by reference to disclose and describe the methods and/or materials in connection with which the publications are cited.

The term "amplicon" as used herein means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase, or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references, each of which are incorporated herein by reference herein in their entirety: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g., "real-time PCR", or "real-time NASBA" as described in Leone et al, Nucleic Acids Research, 26: 2150-2155 (1998), and like references.

As used herein, the term "amplifying" means performing an amplification reaction. A "reaction mixture" means a solution containing all the necessary reactants for performing a reaction, which may include, but is not be limited to, buffering agents to maintain pH at a selected level during a reaction, salts, co-factors, scavengers, and the like.

The terms "fragment" or "segment", as used interchangeably herein, refer to a portion of a larger polynucleotide molecule. A polynucleotide, for example, can be broken up, or fragmented into, a plurality of segments, either through natural processes, as is the case with, e.g., cfDNA fragments that can naturally occur within a biological sample, or through in vitro manipulation. Various methods of fragmenting nucleic acids are well known in the art. These methods may be, for example, either chemical or physical or enzymatic in nature. Enzymatic fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave a polynucleotide at known or unknown locations. Physical fragmentation methods may involve subjecting a polynucleotide to a high shear rate. High shear rates may be produced, for example, by moving DNA through a chamber or channel with pits or spikes, or forcing a DNA sample through a restricted size flow passage, e.g., an aperture having a cross sectional dimension in the micron or submicron range. Other physical methods include sonication and nebulization. Combinations of physical and chemical fragmentation methods may likewise be employed, such as fragmentation by heat and ion-mediated hydrolysis. See, e.g., Sambrook et al., "Molecular Cloning: A Laboratory Manual," 3rd Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range.

The terms "polymerase chain reaction" or "PCR", as used interchangeably herein, mean a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors that are well-known to those of ordinary skill in the art, e.g., exemplified by the following references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including, but not limited to, RT-PCR, real-time PCR, nested PCR, quantitative PCR, multiplexed PCR, and the like. The particular format of PCR being employed is discernible by one skilled in the art from the context of an application. Reaction volumes can range from a few hundred nanoliters, e.g., 200 nL, to a few hundred μL, e.g., 200 μL. "Reverse transcription PCR," or "RT-PCR," means a PCR that is preceded by a reverse transcription reaction that converts a target RNA to a complementary single stranded DNA, which is then amplified, an example of which is described in Tecott et al, U.S. Pat. No. 5,168,038, the disclosure of which is incorporated herein by reference in its entirety. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); the disclosures of which are hereby incorporated by reference herein in their entireties. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Asymmetric PCR" means a PCR wherein one of the two primers employed is in great excess concentration so that the reaction is primarily a linear amplification in which one of the two strands of a target nucleic acid is preferentially copied. The excess concentration of asymmetric PCR primers may be expressed as a concentration ratio. Typical ratios are in the range of from 10 to 100. "Multiplexed PCR" means a PCR wherein multiple target sequences (or a single target sequence and one or more reference sequences) are simultaneously carried out in the same reaction mixture, e.g., Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references, which are incorporated by reference herein in their entireties: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); and Becker-Andre et al, Nucleic Acids Research, 17: 9437-9446 (1989).

The term "primer" as used herein means an oligonucleotide, either natural or synthetic, that is capable, upon forming a duplex with a polynucleotide template, of acting as a point of initiation of nucleic acid synthesis and being extended from its 3'-end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually, primers are extended by a DNA polymerase. Primers usually have a length in the range of from 14 to 40 nucleotides, or in the range of from 18 to 36 nucleotides. Primers are employed in a variety of nucleic acid amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following reference that is incorporated by reference herein in its entirety: Dieffenbach, editor, PCR Primer: A Laboratory Manual, $2^{nd}$ Edition (Cold Spring Harbor Press, New York, 2003).

The terms "unique sequence tag", "sequence tag", "tag" or "barcode", as used interchangeably herein, refer to an oligonucleotide that is attached to a polynucleotide or template molecule and is used to identify and/or track the polynucleotide or template in a reaction or a series of reactions. A sequence tag may be attached to the 3'- or 5'-end of a polynucleotide or template, or it may be inserted into the interior of such polynucleotide or template to form a linear conjugate, sometimes referred to herein as a "tagged polynucleotide," or "tagged template," or the like. Sequence tags may vary widely in size and compositions; the following references, which are incorporated herein by reference in their entireties, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g., via a hybridization reaction or via an enzymatic reaction, such as sequencing; whether they are labeled, e.g., with a fluorescent dye or the like; the number of distinguishable oligonucleotide tags required to unambiguously identify a set of polynucleotides, and the like, and how different the tags of a particular set must be in order to ensure reliable identification, e.g., freedom from cross hybridization or misidentification from sequencing errors. In one aspect, sequence tags can each have a length within a range of from about 2 to about 36 nucleotides, or from about 4 to about 30 nucleotides, or from about 4 to about 20 nucleotides, or from about 8 to about 20 nucleotides, or from about 6 to about 10 nucleotides. In one aspect, sets of sequence tags are used, wherein each sequence tag of a set has a unique nucleotide sequence that differs from that of every other tag of the same set by at least two bases; in another aspect, sets of sequence tags are used wherein the sequence of each tag of a set differs from that of every other tag of the same set by at least three bases. In some embodiments, the unique sequence tag can be a "unique molecular identifier", or "UMI," and can be used, for example, to differentiate various unique nucleic acid sequence fragments originating from the test sample. In other embodiments, a "sequence tag" can be used to differentiate nucleic acid sequence fragments that originate from different test samples (e.g., a sample-specific sequence tag).

The term "enrich" as used herein means to increase a proportion of one or more target nucleic acids, or one or more nucleic acids from a targeted region of a genome, in a sample. An "enriched" sample or sequencing library is therefore a sample or sequencing library in which a proportion of one of more target nucleic acids, or one or more nucleic acids from a targeted region, has been increased with respect to non-target nucleic acids, or regions, in the sample.

The terms "subject" and "patient" are used interchangeably herein and refer to a human or non-human animal who is known to have, or potentially has, a medical condition or disorder, such as, e.g., a cancer.

The term "sequence read" as used herein refers to a nucleotide sequence obtained from or read from a nucleic acid molecule obtained from a subject. Sequence reads can be obtained through various methods known in the art. Generally, sequence reads are obtained post-amplification (e.g., polymerase chain reaction, such as bridge amplification) of a nucleic acid fragment that is obtained or enriched from a test sample.

The term "cell free nucleic acid," "cell free DNA," or "cfDNA," "cell-free RNA," or "cfRNA," refers to nucleic acid fragments that circulate in an individual's body (e.g., in a body fluid such as the bloodstream) and originate from one or more healthy cells and/or from one or more diseased cells (e.g., cancer cells).

The terms "circulating tumor DNA" or "ctDNA" and "circulating tumor RNA" or "ctRNA" refer to nucleic acid fragments (DNA or RNA) that originate from tumor cells or other types of cancer cells, which may be released into a subject's bloodstream as a result of biological processes, such as apoptosis or necrosis of dying cells, or may be actively released by viable tumor cells.

DETAILED DESCRIPTION OF THE INVENTION

Aspects of the invention involve methods for increasing the efficiency of adapter ligation in the preparation of a sequencing library. In accordance with one aspect of the invention, a method utilizes modified nucleotide bases to increase the hybridization properties (e.g., melting temperature (Tm)) of adapter oligonucleotides, and thereby increases the ligation efficiency for ligation of adapters to double-stranded DNA fragments. In one embodiment, an adapter (e.g., a sequencing adapter) has one or more modified nucleotide bases at a 3' end of the adapter. In another aspect, an adapter includes one or more modified nucleotide bases located upstream of a single-stranded 3' base overhang. In still another aspect, an increased interaction between adapters and double-stranded DNA fragments provided by the use of modified nucleotide bases also allows for the use of alternative ligases (e.g., T7 DNA ligase) that cannot typically be used in the preparation of DNA sequencing libraries.

In one embodiment, an adapter is a fork-shaped adapter (e.g., a Y-shaped sequencing adapter) and a modified nucleotide base is a locked nucleic acid (LNA) base (e.g., a T-LNA base) having a higher Tm than a non-modified (e.g., a standard) DNA base. In another embodiment, a modified nucleotide base is a bridged nucleic acid (BNA) base having a higher Tm than a non-modified DNA base. In yet another embodiment, a modified nucleotide base is a super T (5-hydroxybutynl-2'-deoxyuridine) (Integrated DNA Technologies). In still another embodiment, a modified base is a C-5 propynyl-U or a 2'-Omethyl. In other embodiments, an adapter can be a hairpin adapter, a linear adapter, or any other known adapter.

In another embodiment, one or more modified bases can be added to an adapter or to a double-stranded DNA (dsDNA) fragment through a polymerization reaction (e.g., using a DNA polymerase). For example, a modified 3' A tail base can be added to a DNA fragment using a DNA polymerase, and can stabilize an interaction between the adapter and the dsDNA fragment, and as a result, leads to a higher ligation efficiency. In general, any known DNA polymerase can be used in connection with the methods described herein.

Figure 1:
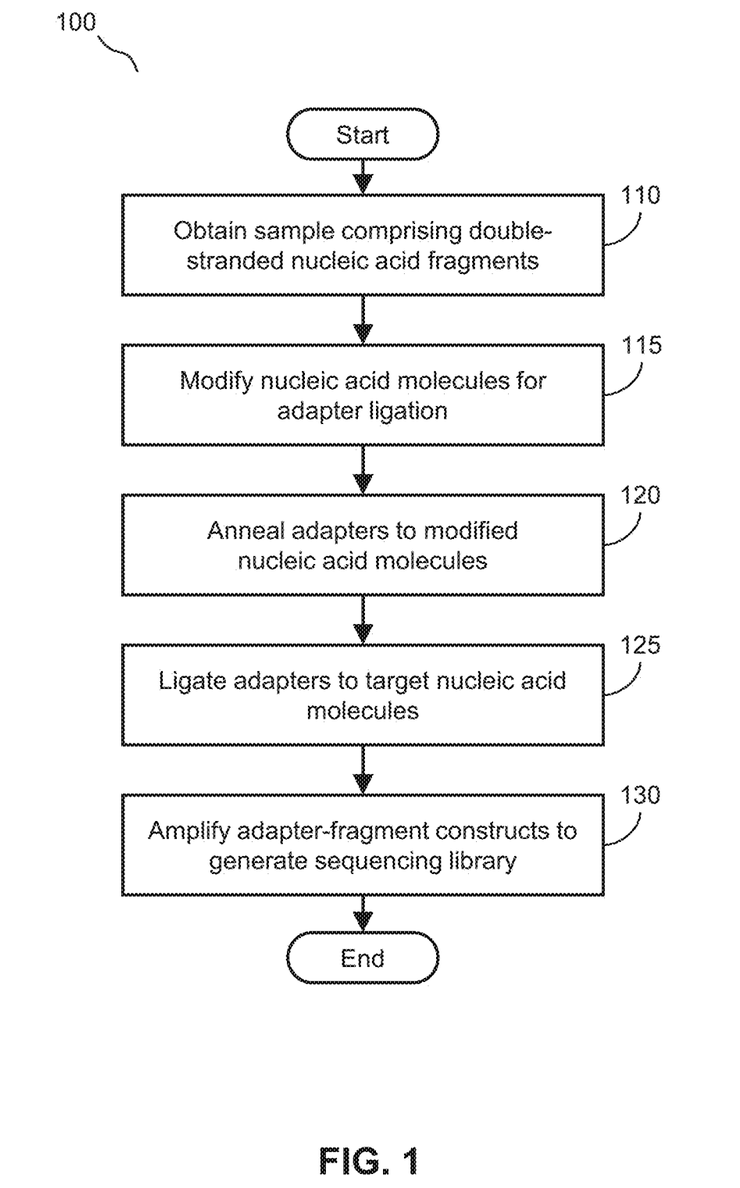
FIG. 1 is a flow diagram illustrating of a method for increasing ligation efficiency in the preparation of a sequencing library, in accordance with one embodiment of the present invention.

FIG. 1 is a flow diagram illustrating an example of a method 100 for increasing a ligation efficiency in the preparation of a sequencing library. As shown in FIG. 1, method 100 utilizes Y-shaped sequencing adapters ("Y-adapters") that include at least one modified nucleotide base. As noted above, in other embodiments, the adapters can be hairpin adapters, linear adapters, or any other known adapters. In accordance with some embodiments of the invention, at least one modified nucleotide base has an increased melting temperature compared to a non-modified DNA base. The use of at least one modified nucleotide base having a higher Tm than a non-modified DNA base improves hybridization between an annealed adapter and a double-stranded nucleic acid (dsNA) molecule (e.g., a targeted dsDNA molecule or fragment), thereby increasing the efficiency of adapter ligation to double-stranded nucleic acid molecules. Method 100 may include, but is not limited to, the following steps.

At step 110, a sample comprising double-stranded target nucleic acid (dsNA) fragments or molecules (or targeted dsDNA fragments) is obtained. The sample can be, for example, a fragmented genomic DNA sample, a cDNA sample reverse transcribed from RNA and subsequently converted to a double strand DNA molecule, or a cell-free nucleic acid (e.g., cfDNA) sample. The ends of the double stranded nucleic acid molecules in the sample may include, for example, varying 5' and 3' overhangs, blunt-ends, and all possible combinations thereof.

At step 115, the double-stranded nucleic acid molecules are modified for adapter ligation. In one embodiment, an end repair reaction is performed to repair any overhanging ends and gaps in the nucleic acid molecules and to phosphorylate the 5' ends of the molecules. A single "A" deoxynucleotide is then added to both 3' ends of the nucleic acid molecules producing a single-base 3' A overhang.

At step 120, adapters (e.g., Y-adapters) that include at least one modified nucleotide base are annealed to the modified nucleic acid molecules. For example, in one embodiment, an adapter having a single T-LNA nucleotide at the 3'-end of the adapter is used. In another embodiment, the adapter can include one or more modified bases located upstream of a single-stranded 3' base overhang (e.g., immediately before a single-stranded 3' base overhang). The presence of a modified T nucleotide stabilizes the base pairing between an A on a nucleic acid molecule and the modified T on the sequencing adapter, which allows for higher ligation efficiency (e.g., similar to the efficiency of a traditional "sticky end" ligation). Exemplified Y-adapters that include at least one modified nucleotide are described in more detail with reference to FIGS. 2A and 2B.

At step 125, the adapters are ligated to the modified nucleic acid molecules to form adapter-fragment constructs (also referred to herein as "adapter-target constructs"). The ligation reaction can be performed using any suitable ligase enzyme which joins two copies of the adapter to each nucleic acid molecule (i.e., one at each end) to form an adapter-fragment construct. In one embodiment, a ligation reaction is performed using T4 DNA ligase. In another embodiment, T7 DNA ligase is used for adapter ligation to the modified nucleic acid molecule. At step 130, the adapter-fragment constructs are amplified to generate a sequencing library.

Figure 2A:
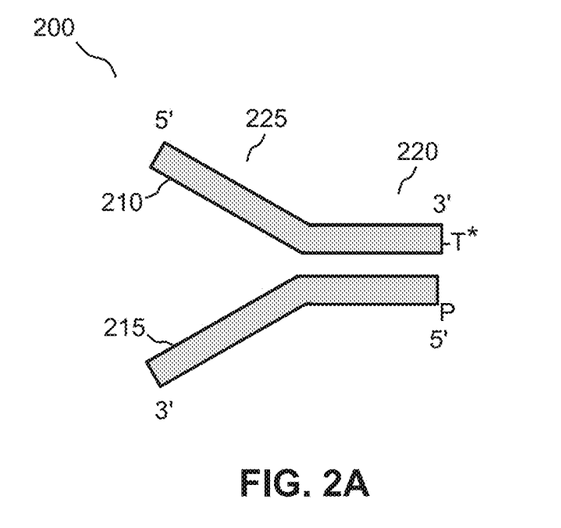
FIGS. 2A and 2B are schematic diagrams of a Y-adapter that includes a 3' T-LNA overhang and a Y-adapter that includes an LNA inserted 5' to a standard 3' T overhang, respectively, in accordance with one embodiment of the present invention.
Figure 2B:
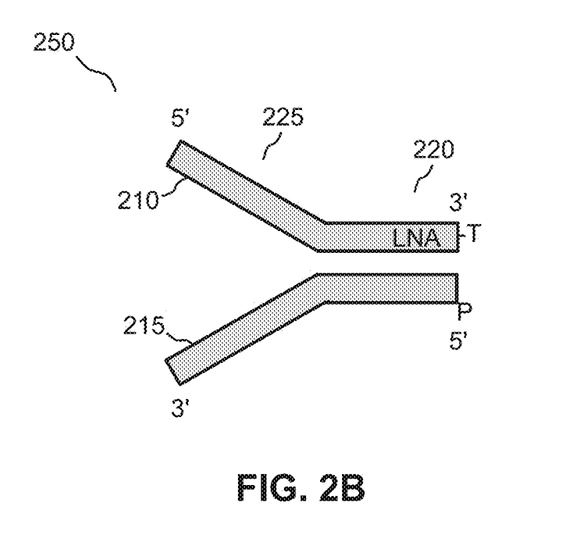

FIGS. 2A and 2B illustrate schematic diagrams of an exemplified Y-adapter 200 that includes a modified 3' T base overhang and an exemplified Y-adapter 250 that includes a modified 3' T LNA base, respectively. In other embodiments, as noted elsewhere herein, the adapters can be hairpin adapters, linear adapters, or any other known adapters. Referring to FIG. 2A, Y-adapter 200 comprises two partially complementary oligonucleotides, oligonucleotide 210 and oligonucleotide 215, which form a Y-shaped (forked) adapter when annealed. The 5' end of oligonucleotide 215 is complementary to a portion of a sequence in oligonucleotide 210. Oligonucleotide 210 includes a single modified T base overhang at the 3' end (indicated by T*). In one embodiment, the modified T base is an LNA base. The 5' end of oligonucleotide 215 is phosphorylated (indicated by "P"). Annealing of oligonucleotides 210 and 215 form a double-stranded region 220 and a single-stranded unmatched region 225.

Referring to FIG. 2B, Y-adapter 250 is substantially the same as Y-adapter 200 except that oligonucleotide 210 includes one or more modified bases (e.g., as shown, one or more LNA bases (indicated by "LNA")) inserted immediately before a single stranded 3' T base overhang. Because oligonucleotide 210 includes at least one modified nucleotide (e.g., one or more LNA base) in a portion of a sequence that is complementary to oligonucleotide 215, double-stranded region 220 has a more stable duplex structure (e.g., the double-stranded region doesn't "breathe" as much) and is therefore a better substrate for an enzyme-catalyzed ligation reaction.

Figure 3:
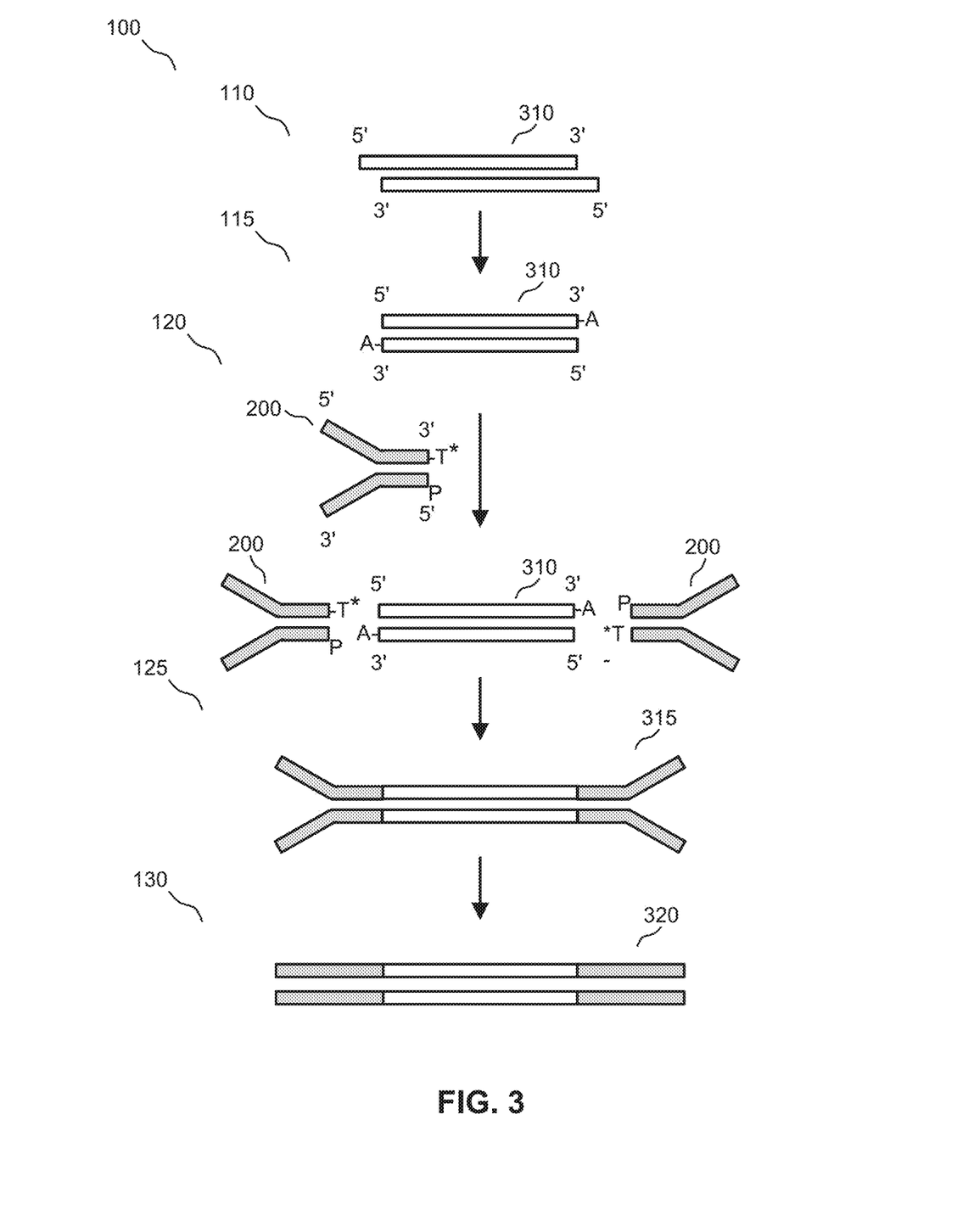
FIG. 3 shows pictorially the steps of the method of FIG. 1.

FIG. 3 shows pictorially the steps of method 100 of FIG. 1. Namely, at step 110, a sample comprising double-stranded target nucleic acid molecules is obtained. In the depicted example, a single double-stranded target nucleic acid molecule 310 with free 5' end overhangs is shown.

At step 115, target nucleic acid molecule 310 is modified for adapter ligation. The ends of target nucleic acid molecule 310 are end repaired using, for example, T4 DNA polymerase and Klenow polymerase and phosphorylated with a polynucleotide kinase enzyme. A single "A" deoxynucleotide is then added to both 3' ends of target nucleic acid molecule 310 using, for example, a Taq polymerase enzyme, producing a single base 3' overhang that is complementary to a modified 3' base (indicated in FIG. 3 as T*) overhang on double-stranded region 220 of Y-adapter 200.

At step 120, an adapter 200 (exemplified here as a Y-adapter) is annealed to target nucleic acid molecule 310. Because of the modified 3' T* base on oligonucleotide 210, the base pairing between the 3' A overhang on target nucleic acid molecule 310 and the modified T* Y-adapter 200 is stabilized, which provides for a higher ligation efficiency.

At step 125, Y-adapter 200 is ligated to target nucleic acid molecule 310. The ligation reaction can be performed using any suitable ligase enzyme which joins two copies of Y-adapter 200 to target nucleic acid molecule 310 (i.e., one at each end) to form an adapter-target construct 315 with the Y-adapter 200 and the target nucleic acid molecule 310. In one embodiment, the ligation reaction is performed using T4 DNA ligase.

At step 130, the adapter-target construct 315 is amplified to generate a sequencing library molecule 320 and sequenced for subsequent analysis.

Figure 4:
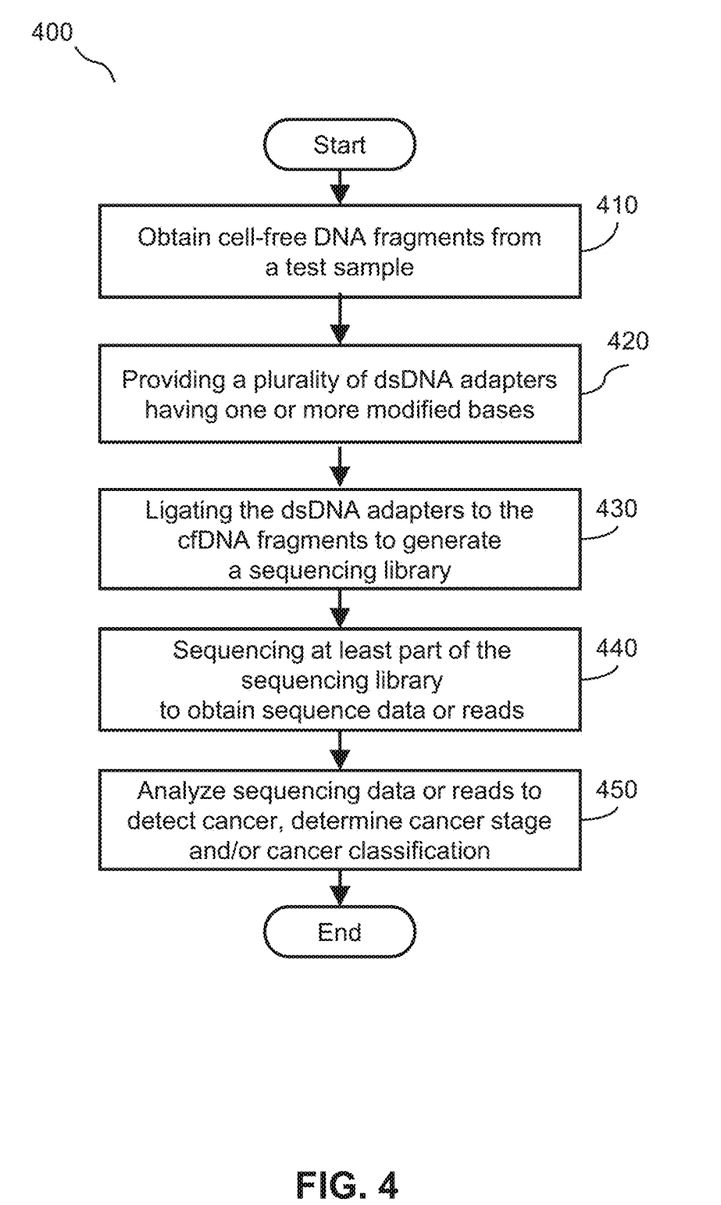
FIG. 4 is a flow diagram illustrating a method for preparing a sequencing library from a cell-free DNA test sample for use in detecting cancer, determining cancer status, monitoring cancer progression, and/or determining a cancer classification.

FIG. 4 is a flow diagram illustrating a method 400 for preparing a sequencing library from a cell-free DNA test sample for use in detecting cancer, determining cancer status, monitoring cancer progression, and/or determining a cancer classification.

As shown in FIG. 4, at step 410, a biological test sample is obtained from a subject (e.g., a patient) known to have or suspected of having cancer. As described further herein, a biological test sample can be a sample selected from the group consisting of blood, plasma, serum, urine and saliva samples. In other embodiments, the sample is a plasma sample from a cancer patient, or a patient suspected of having cancer. Alternatively, as noted above, the biological sample may comprise a sample selected from the group consisting of whole blood, a blood fraction, a tissue biopsy, pleural fluid, pericardial fluid, cerebral spinal fluid, and peritoneal fluid. In accordance with some embodiments, the biological test sample comprises a plurality of cell-free nucleic acids (e.g., cell-free DNA (cfDNA)) fragments originating from healthy cells and from cancer cells. Optionally, in one embodiment, cell-free nucleic acids (e.g., cfDNA) can be extracted and/or purified from the biological test sample before proceeding with subsequent library preparation steps. In general, any method known in the art can be used to extract and purify cell-free nucleic acids from the biological test sample. For example, cell-free nucleic acids can be extracted and purified using one or more known commercially available protocols or kits, such as the QIAAMP® circulating nucleic acid kit (Qiagen). Furthermore, as noted above, nucleic acid molecules can be modified for adapter ligation. For example, in some embodiments, an end repair reaction is performed to repair any overhanging ends and gaps in the target nucleic acid molecules and phosphorylate the 5' ends of the molecules. A single "A" deoxynucleotide is then added to both 3' ends of the target nucleic acid molecules producing a single-base 3' A overhang.

At step 420, a plurality of double-stranded DNA adapters are provided, having one or more modified bases. As noted above, in one embodiment, an adapter has one or more modified nucleotides at the 3' end of the adapter. In another embodiment, an adapter includes one or more modified nucleotide bases located upstream of a single-stranded 3' base overhang (e.g., immediately before a single-stranded 3' base overhang). In some embodiments, an adapter can be a sequencing adapter (e.g., a Y-shaped sequencing adapter). In other embodiments, an adapter can be a hairpin adapter, a linear adapter, or any other known adapters.

In one embodiment, sequencing adapters can include a unique molecular identifier (UMI) sequence, such that, after library preparation, the sequencing library will include UMI-tagged amplicons derived from cell-free nucleic acid fragments. In one embodiment, as described in further detail elsewhere herein, unique sequence tags (e.g., unique molecular identifiers (UMIs)) can be used to identify unique nucleic acid sequences from a cell-free nucleic acid sample. For example, differing unique sequence tags (UMIs) can be used to differentiate various unique nucleic acid sequence fragments originating from the test sample. In another embodiment, unique sequence tags (UMIs) can be used to reduce amplification bias, which is the asymmetric amplification of different targets due to differences in nucleic acid composition (e.g., high GC content). The unique sequence tags (UMIs) can also be used to discriminate between nucleic acid mutations that arise during amplification. The unique sequence tags can be present in a multi-functional nucleic acid adapter, which adapter can comprise both a unique sequence tag and a universal priming site. In one embodiment, the unique sequence tag can comprise a short oligonucleotide sequence having a length that ranges from about 2 nt to about 100 nt, such as from about 2 nt to about 60 nt, such as from about 2 to about 40 nt, or such as from about 2 to about 20 nt. In another embodiment, a UMI tag can comprise a short oligonucleotide sequence greater than about 5, 6, 7, 8, 9, 10, 11, 12, 13, 14, 15, 16, 17, or 18 nucleotides (nt) in length.

In another embodiment, an adapter can include a universal primer and/or one or more sequencing oligonucleotides for use in subsequent cluster generation and/or sequencing (e.g., known P5 and P7 sequences for used in sequencing by synthesis (SBS) (Illumina, San Diego, Calif.)).

At step 430, the adapters, obtained from step 450, having one or more modified nucleotide bases, are annealed to a plurality of cell-free DNA (cfDNA) fragments obtained from the biological test sample at step 410. For example, in one embodiment, the adapters include a single nucleotide at the 3'-end of the double-stranded region of the adapter that is complementary to, and hybridizes with, a single nucleotide 5'-end of the cfDNA fragment. In another embodiment, the adapter can include one or more modified bases inserted into the double-stranded region of the adapter immediately before a single-stranded 3' base overhang that is complementary to, and hybridizes with, the 5'-end of the cfDNA fragment. In certain aspects of the invention, the presence of one or more modified nucleotide bases stabilizes the base pairing between an adapter and a cfDNA fragment, which allows for higher ligation efficiency (e.g., similar to the efficiency of a traditional "sticky end" ligation).

After annealing of the adapters to the cfDNA fragments, the adapters are ligated to the cfDNA fragment molecules to form adapter-template constructs. The ligation reaction can be performed using any suitable ligase enzyme that joins two copies of the adapter to each target nucleic acid molecule (i.e., one at each end) to form an adapter-target construct. For example, in one embodiment, the ligation reaction is performed using T4 DNA ligase. In another embodiment, T7 DNA ligase is used for ligation of the adapter to the cfDNA fragments. After ligation, the adapter-template constructs can be amplified to generate a sequencing library.

At step 440, at least a portion of a sequence library is sequenced to obtain sequencing data or sequence reads. In general, any method known in the art can be used to obtain sequence data or sequence reads from a test sample. For example, in one embodiment, sequencing data or sequence reads from a cell-free DNA sample can be acquired using next generation sequencing (NGS). Non-limiting examples of next-generation sequencing methods include sequencing by synthesis technology (Illumina), pyrosequencing (454), ion semiconductor technology (Ion Torrent sequencing), single-molecule real-time sequencing (Pacific Biosciences), sequencing by ligation (SOLiD sequencing), and nanopore sequencing (Oxford Nanopore Technologies). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. In still another embodiment, sequencing is paired-end sequencing. Optionally, an amplification step is performed prior to sequencing. In certain embodiments, the sequencing comprises whole genome sequencing (or shotgun sequencing) of the cfDNA library to provide sequence data or sequencing reads representative of a whole genome. In other embodiments, the sequencing comprises targeted sequencing of the cfDNA library. For example, the sequencing library can be enriched for specific target sequences (e.g., using a plurality of hybridization probes to isolate cfDNA fragments known to be, or suspected of being, indicative of cancer) and the targeted sequences sequenced.

At step 450, the sequencing data or sequencing reads can be analyzed for detecting the presence or absence of cancer, determining cancer stage, monitoring cancer progression, and/or for determining a cancer classification (e.g., cancer type or cancer tissue of origin). In another embodiment, the sequencing data or reads can be used to infer the presence or absence of cancer, cancer status and/or a cancer classification. For example, the sequencing data or sequencing reads can be analyzed to identify one or more mutational signatures indicative of cancer (see, e.g., PCT Application No. PCT/US2017/060472, filed Nov. 7, 2017). Alternatively, the sequencing data or sequencing reads can be modeled for the detection and/or classification of cancer (see, e.g., U.S. Patent Application No. 62/363,047, filed Feb. 27, 2018, or U.S. Patent Application No. 62/642,301, filed Mar. 13, 2018).

In one embodiment, the sequencing data or sequencing reads can be analyzed to detect the presence or absence of, determine the stage of, monitor progression of, and/or classify a carcinoma, a sarcoma, a myeloma, a leukemia, a lymphoma, a blastoma, a germ cell tumor, or any combination thereof. In some embodiments, the carcinoma may be an adenocarcinoma. In other embodiments, the carcinoma may be a squamous cell carcinoma. In still other embodiments, the carcinoma is selected from the group consisting of: small cell lung, non-small-cell lung, nasopharyngeal, colorectal, anal, liver, urinary bladder, cervical, testicular, ovarian, gastric, esophageal, head-and-neck, pancreatic, prostate, renal, thyroid, melanoma, and breast carcinoma. In another embodiment, the sequencing data or sequencing reads can be analyzed to detect a presence or absence of, determine the stage of, monitor progression of, and/or classify a sarcoma. In certain embodiments, the sarcoma can be selected from the group consisting of: osteosarcoma, chondrosarcoma, leiomyosarcoma, rhabdomyosarcoma, mesothelial sarcoma (mesothelioma), fibrosarcoma, angiosarcoma, liposarcoma, glioma, and astrocytoma. In still another embodiment, the sequencing data or sequencing reads can be analyzed to detect a presence or absence of, determine the stage of, monitor progression of, and/or classify leukemia. In certain embodiments, the leukemia can be selected from the group consisting of: myelogenous, granulocytic, lymphatic, lymphocytic, and lymphoblastic leukemia. In still another embodiment, the sequencing data or sequencing reads can be used to detect a presence or absence of, determine the stage of, monitor progression of, and/or classify a lymphoma. In certain embodiments, the lymphoma can be selected from the group consisting of: Hodgkin's lymphoma and Non-Hodgkin's lymphoma.

Sequencing and Bioinformatics

As reviewed above, aspects of the invention include sequencing of nucleic acid molecules to generate a plurality of sequence reads, compilation of a plurality of sequence reads into a sequencing library, and bioinformatic manipulation of the sequence reads and/or sequencing library to determine sequence information from a test sample (e.g., a biological sample). In some embodiments, one or more aspects of the subject methods are conducted using a suitably-programmed computer system, as described further herein.

In certain embodiments, a sample is collected from a subject, followed by enrichment for genetic regions or genetic fragments of interest. For example, in some embodiments, a sample can be enriched by hybridization to a nucleotide array comprising cancer-related genes or gene fragments of interest. In some embodiments, a sample can be enriched for genes of interest (e.g., cancer-associated genes) using other methods known in the art, such as hybrid capture. See, e.g., Lapidus (U.S. Pat. No. 7,666,593), the contents of which is incorporated by reference herein in its entirety. In one hybrid capture method, a solution-based hybridization method is used that includes the use of biotinylated oligonucleotides and streptavidin coated magnetic beads. See, e.g., Duncavage et al., J Mol Diagn. 13(3): 325-333 (2011); and Newman et al., Nat Med. 20(5): 548-554 (2014). Isolation of nucleic acid from a sample in accordance with the methods of the invention can be done according to any method known in the art.

Sequencing may be by any method or combination of methods known in the art. For example, known DNA sequencing techniques include, but are not limited to, classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, Polony sequencing, and SOLiD sequencing. Sequencing of separated molecules has more recently been demonstrated by sequential or single extension reactions using polymerases or ligases as well as by single or sequential differential hybridizations with libraries of probes.

One conventional method to perform sequencing is by chain termination and gel separation, as described by Sanger et al., Proc Natl. Acad. Sci. USA, 74(12): 5463 67 (1977), the contents of which are incorporated by reference herein in their entirety. Another conventional sequencing method involves chemical degradation of nucleic acid fragments. See, Maxam et al., Proc. Natl. Acad. Sci., 74: 560 564 (1977), the contents of which are incorporated by reference herein in their entirety. Methods have also been developed based upon sequencing by hybridization. See, e.g., Harris et al., (U.S. patent application number 2009/0156412), the contents of which are incorporated by reference herein in their entirety.

A sequencing technique that can be used in the methods of the provided invention includes, for example, Helicos True Single Molecule Sequencing (tSMS) (Harris T. D. et al. (2008) Science 320:106-109), the contents of which are incorporated by reference herein in their entirety. Further description of tSMS is shown, for example, in Lapidus et al. (U.S. Pat. No. 7,169,560), the contents of which are incorporated by reference herein in their entirety, Lapidus et al. (U.S. patent application publication number 2009/0191565, the contents of which are incorporated by reference herein in their entirety), Quake et al. (U.S. Pat. No. 6,818,395, the contents of which are incorporated by reference herein in their entirety), Harris (U.S. Pat. No. 7,282,337, the contents of which are incorporated by reference herein in their entirety), Quake et al. (U.S. patent application publication number 2002/0164629, the contents of which are incorporated by reference herein in their entirety), and Braslaysky, et al., PNAS (USA), 100: 3960-3964 (2003), the contents of which are incorporated by reference herein in their entirety.

Another example of a DNA sequencing technique that can be used in the methods of the provided invention is 454 sequencing (Roche) (Margulies, M et al. 2005, Nature, 437, 376-380, the contents of which are incorporated by reference herein in their entirety). Another example of a DNA sequencing technique that can be used in the methods of the provided invention is SOLiD technology (Applied Biosystems). Another example of a DNA sequencing technique that can be used in the methods of the provided invention is Ion Torrent sequencing (U.S. patent application publication numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982, the contents of each of which are incorporated by reference herein in their entirety).

In some embodiments, the sequencing technology is Illumina sequencing. Illumina sequencing is based on the amplification of DNA on a solid surface using fold-back PCR and anchored primers. Genomic DNA can be fragmented, or in the case of cfDNA, fragmentation is not needed due to the already short fragments. Adapters are ligated to the 5'- and 3'-ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. Yet another example of a sequencing technique that can be used in the methods of the provided invention is nanopore sequencing (Soni G V and Meller A. (2007) Clin Chem 53: 1996-2001, the contents of which are incorporated by reference herein in their entirety). Another example of a sequencing technique that can be used in the methods of the provided invention involves using a chemical-sensitive field effect transistor (chemFET) array to sequence DNA (for example, as described in US Patent Application Publication No. 20090026082, the contents of which are incorporated by reference herein in their entirety). Another example of a sequencing technique that can be used in the methods of the provided invention involves using an electron microscope (Moudrianakis E. N. and Beer M. Proc Natl Acad Sci USA. 1965 March; 53:564-71, the contents of which are incorporated by reference herein in their entirety).

If the nucleic acid from the sample is degraded or only a minimal amount of nucleic acid can be obtained from the sample, PCR can be performed on the nucleic acid in order to obtain a sufficient amount of nucleic acid for sequencing (See, e.g., Mullis et al. U.S. Pat. No. 4,683,195, the contents of which are incorporated by reference herein in its entirety).

Biological Samples

Aspects of the invention involve obtaining a test sample, e.g., a biological sample, such as a tissue and/or body fluid sample, from a subject for purposes of analyzing a plurality of nucleic acids (e.g., a plurality of RNA molecules) therein. Samples in accordance with embodiments of the invention can be collected in any clinically-acceptable manner Any test sample suspected of containing a plurality of nucleic acids can be used in conjunction with the methods of the present invention. In some embodiments, a test sample can comprise a tissue, a body fluid, or a combination thereof. In some embodiments, a biological sample is collected from a healthy subject. In some embodiments, a biological sample is collected from a subject who is known to have a particular disease or disorder (e.g., a particular cancer or tumor). In some embodiments, a biological sample is collected from a subject who is suspected of having a particular disease or disorder.

As used herein, the term "tissue" refers to a mass of connected cells and/or extracellular matrix material(s). Non-limiting examples of tissues that are commonly used in conjunction with the present methods include skin, hair, finger nails, endometrial tissue, nasal passage tissue, central nervous system (CNS) tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or non-human mammal. Tissue samples in accordance with embodiments of the invention can be prepared and provided in the form of any tissue sample types known in the art, such as, for example and without limitation, formalin-fixed paraffin-embedded (FFPE), fresh, and fresh frozen (FF) tissue samples.

As used herein, the term "body fluid" refers to a liquid material derived from a subject, e.g., a human or non-human mammal. Non-limiting examples of body fluids that are commonly used in conjunction with the present methods include mucous, blood, plasma, serum, serum derivatives, synovial fluid, lymphatic fluid, bile, phlegm, saliva, sweat, tears, sputum, amniotic fluid, menstrual fluid, vaginal fluid, semen, urine, cerebrospinal fluid (CSF), such as lumbar or ventricular CSF, gastric fluid, a liquid sample comprising one or more material(s) derived from a nasal, throat, or buccal swab, a liquid sample comprising one or more materials derived from a lavage procedure, such as a peritoneal, gastric, thoracic, or ductal lavage procedure, and the like.

In some embodiments, a test sample can comprise a fine needle aspirate or biopsied tissue. In some embodiments, a test sample can comprise media containing cells or biological material. In some embodiments, a test sample can comprise a blood clot, for example, a blood clot that has been obtained from whole blood after the serum has been removed. In some embodiments, a test sample can comprise stool. In one preferred embodiment, a test sample is drawn whole blood. In one aspect, only a portion of a whole blood sample is used, such as plasma, red blood cells, white blood cells, and platelets. In some embodiments, a test sample is separated into two or more component parts in conjunction with the present methods. For example, in some embodiments, a whole blood sample is separated into plasma, red blood cell, white blood cell, and platelet components.

In some embodiments, a test sample includes a plurality of nucleic acids not only from the subject from which the test sample was taken, but also from one or more other organisms, such as viral DNA/RNA that is present within the subject at the time of sampling.

Nucleic acid can be extracted from a test sample according to any suitable methods known in the art, and the extracted nucleic acid can be utilized in conjunction with the methods described herein. See, e.g., Maniatis, et al., Molecular Cloning: A Laboratory Manual, Cold Spring Harbor, N.Y., pp. 280-281, 1982, the contents of which are incorporated by reference herein in their entirety.

In one preferred embodiment, cell free nucleic acid (e.g., cell-free DNA (cfDNA) and/or cell-free RNA (cfRNA)) are extracted from a test sample. cfDNA are short base nuclear-derived DNA fragments present in several bodily fluids (e.g. plasma, stool, urine). See, e.g., Mouliere and Rosenfeld, PNAS 112(11): 3178-3179 (March 2015); Jiang et al., PNAS (March 2015); and Mouliere et al., Mol Oncol, 8(5):927-41 (2014). Tumor-derived circulating tumor nucleic acids (e.g., ctDNA and/or ctRNA) constitutes a minority population of cfNAs (i.e., cfDNA and/or cfRNA), in some cases, varying up to about 50%. In some embodiments, ctDNA and/or ctRNA varies depending on tumor stage and tumor type. In some embodiments, ctDNA and/or ctRNA varies from about 0.001% up to about 30%, such as about 0.01% up to about 20%, such as about 0.01% up to about 10%. The covariates of ctDNA and/or ctRNA are not fully understood, but appear to be positively correlated with tumor type, tumor size, and tumor stage. E.g., Bettegowda et al, Sci Trans Med, 2014; Newmann et al, Nat Med, 2014. Despite the challenges associated with the low population of ctDNA/ctRNA in cfNAs, tumor variants have been identified in ctDNA and/or ctRNA across a wide span of cancers. E.g., Bettegowda et al, Sci Trans Med, 2014. Furthermore, analysis of cfDNA and/or cfRNA versus tumor biopsy is less invasive, and methods for analyzing, such as sequencing, enable the identification of sub-clonal heterogeneity. Analysis of cfDNA and/or cfRNA has also been shown to provide for more uniform genome-wide sequencing coverage as compared to tumor tissue biopsies. In some embodiments, a plurality of cfDNA and/or cfRNA are extracted from a sample in a manner that reduces or eliminates co-mingling of cfDNA and genomic DNA. For example, in some embodiments, a sample is processed to isolate a plurality of the cfDNA and/or cfRNA therein in less than about 2 hours, such as less than about 1.5, 1 or 0.5 hours.

A non-limiting example of a procedure for preparing nucleic acid from a blood sample follows. Blood may be collected in 10 mL EDTA tubes (for example, the BD VACUTAINER® family of products from Becton Dickinson, Franklin Lakes, N.J.), or in collection tubes that are adapted for isolation of cfDNA (for example, the CELL FREE DNA BCT® family of products from Streck, Inc., Omaha, Nebr.) can be used to minimize contamination through chemical fixation of nucleated cells, but little contamination from genomic DNA is observed when samples are processed within 2 hours or less, as is the case in some embodiments of the present methods. Beginning with a blood sample, plasma may be extracted by centrifugation, e.g., at 3000 rpm for 10 minutes at room temperature minus brake. Plasma may then be transferred to 1.5 ml tubes in 1 ml aliquots and centrifuged again at 7000 rpm for 10 minutes at room temperature. Supernatants can then be transferred to new 1.5 ml tubes. At this stage, samples can be stored at −80° C. In certain embodiments, samples can be stored at the plasma stage for later processing, as plasma may be more stable than storing extracted cfDNA and/or cfRNA.

Plasma DNA and/or RNA can be extracted using any suitable technique. For example, in some embodiments, plasma DNA and/or RNA can be extracted using one or more commercially available assays, for example, the QIAmp Circulating Nucleic Acid Kit family of products (Qiagen N.V., Venlo Netherlands). In certain embodiments, the following modified elution strategy may be used. DNA and/or RNA may be extracted using, e.g., a QIAmp Circulating Nucleic Acid Kit, following the manufacturer's instructions (maximum amount of plasma allowed per column is 5 mL). If cfDNA and/or cfRNA are being extracted from plasma where the blood was collected in Streck tubes, the reaction time with proteinase K may be doubled from 30 min to 60 min Preferably, as large a volume as possible should be used (i.e., 5 mL). In various embodiments, a two-step elution may be used to maximize cfDNA and/or cfRNA yield. First, DNA and/or RNA can be eluted using 30 µL of buffer AVE for each column. A minimal amount of buffer necessary to completely cover the membrane can be used in the elution in order to increase cfDNA and/or cfRNA concentration. By decreasing dilution with a small amount of buffer, downstream desiccation of samples can be avoided to prevent melting of double stranded DNA or material loss. Subsequently, about 30 µL of buffer for each column can be eluted. In some embodiments, a second elution may be used to increase DNA and/or RNA yield.

In other embodiments, RNA can be extracted and/or isolated using any suitable technique. For example, in some embodiments, RNA can be extracted using a commercially-available kit and/or protocol, e.g., a QIAamp Circulating Nucleic Acids kit and micro RNA extraction protocol.

In some embodiments, the methods involve DNase treating an extracted nucleic acid sample to remove cell-free DNA from a mixed cfDNA and cfRNA test sample.

Computer Systems and Devices

Aspects of the invention described herein can be performed using any type of computing device, such as a computer, that includes a processor, e.g., a central processing unit, or any combination of computing devices where each device performs at least part of the process or method.

In some embodiments, systems and methods described herein may be performed with a handheld device, e.g., a smart tablet, or a smart phone, or a specialty device produced for the system.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Processors suitable for the execution of computer programs include, by way of example, both general and special purpose microprocessors, and any one or more processors of any kind of digital computer. Generally, a processor will receive instructions and data from a read-only memory or a random access memory, or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including, by way of example, semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected through a network by any form or medium of digital data communication, e.g., a communication network. For example, a reference set of data may be stored at a remote location and a computer can communicate across a network to access the reference data set for comparison purposes. In other embodiments, however, a reference data set can be stored locally within the computer, and the computer accesses the reference data set within the CPU for comparison purposes. Examples of communication networks include, but are not limited to, cell networks (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, a data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a file or a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over a network (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

Suitable computing devices typically include mass memory, at least one graphical user interface, at least one display device, and typically include communication between devices. The mass memory illustrates a type of computer-readable media, namely computer storage media. Computer storage media may include volatile, nonvolatile, removable, and non-removable media implemented in any method or technology for storage of information, such as computer readable instructions, data structures, program modules, or other data. Examples of computer storage media include RAM, ROM, EEPROM, flash memory, or other memory technology, CD-ROM, digital versatile disks (DVD) or other optical storage, magnetic cassettes, magnetic tape, magnetic disk storage or other magnetic storage devices, Radiofrequency Identification (RFID) tags or chips, or any other medium that can be used to store the desired information, and which can be accessed by a computing device.

Functions described herein can be implemented using software, hardware, firmware, hardwiring, or combinations of any of these. Any of the software can be physically located at various positions, including being distributed such that portions of the functions are implemented at different physical locations.

As one skilled in the art would recognize as necessary or best-suited for performance of the methods of the invention, a computer system for implementing some or all of the described inventive methods can include one or more processors (e.g., a central processing unit (CPU) a graphics processing unit (GPU), or both), main memory and static memory, which communicate with each other via a bus.

A processor will generally include a chip, such as a single core or multi-core chip, to provide a central processing unit (CPU). A process may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer system. Preferably, each computer includes a non-transitory memory such as a solid state drive, flash drive, disk drive, hard drive, etc.

While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to, one or more solid-state memories (e.g., subscriber identity module (SIM) card, secure digital card (SD card), micro SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

Any of the software can be physically located at various positions, including being distributed such that portions of the functions are implemented at different physical locations.

Additionally, systems of the invention can be provided to include reference data. Any suitable genomic data may be stored for use within the system. Examples include, but are not limited to: comprehensive, multi-dimensional maps of the key genomic changes in major types and subtypes of cancer from The Cancer Genome Atlas (TCGA); a catalog of genomic abnormalities from The International Cancer Genome Consortium (ICGC); a catalog of somatic mutations in cancer from COSMIC; the latest builds of the human genome and other popular model organisms; up-to-date reference SNPs from dbSNP; gold standard indels from the 1000 Genomes Project and the Broad Institute; exome capture kit annotations from Illumina, Agilent, Nimblegen, and Ion Torrent; transcript annotations; small test data for experimenting with pipelines (e.g., for new users).

In some embodiments, data is made available within the context of a database included in a system. Any suitable database structure may be used including relational databases, object-oriented databases, and others. In some embodiments, reference data is stored in a relational database such as a "not-only SQL" (NoSQL) database. In certain embodiments, a graph database is included within systems of the invention. It is also to be understood that the term "database" as used herein is not limited to one single database; rather, multiple databases can be included in a system. For example, a database can include two, three, four, five, six, seven, eight, nine, ten, fifteen, twenty, or more individual databases, including any integer of databases therein, in accordance with embodiments of the invention. For example, one database can contain public reference data, a second database can contain test data from a patient, a third database can contain data from healthy individuals, and a fourth database can contain data from sick individuals with a known condition or disorder. It is to be understood that any other configuration of databases with respect to the data contained therein is also contemplated by the methods described herein.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof. All references cited throughout the specification are expressly incorporated by reference herein.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

What is claimed is:

1. A method for preparing a sequencing library from a test sample comprising a plurality of double-stranded DNA fragments, the method comprising the steps:
   (a) obtaining a test sample comprising a plurality of double-stranded DNA (dsDNA) fragments, wherein the dsDNA fragments each comprise a forward strand and a reverse strand;
   (b) contacting the test sample with a plurality of dsDNA adapters, wherein the dsDNA adapters comprise a single stranded 3' T base overhang, wherein the single stranded 3' T base overhang, or one or more bases located immediately upstream of the single stranded 3' T base overhang, has a melting temperature that is higher than a melting temperature of a non-modified DNA base, wherein the single stranded 3' T base overhang, or the one or more bases located immediately upstream of the single stranded 3' T base overhang, are selected from the group consisting of: locked nucleic acid (LNA) bases, bridged nucleic acid (BNA) bases, super T (5-hydroxybutynl-2'-deoxyuridine), C-5 propynyl-U, or any combination thereof;
   (c) ligating the dsDNA adapters to the dsDNA fragments to create a plurality of dsDNA adapter-fragment constructs; and
   (d) amplifying the dsDNA adapter-fragment constructs to generate a sequencing library.

2. The method according to claim 1, wherein the method further comprises:
   (a) sequencing the library to obtain a plurality of sequence reads; and
   (b) analyzing the plurality of sequence reads to detect the presence or absence of cancer, determine cancer status, monitor cancer progression and/or determine a cancer classification in the subject.

3. The method according to claim 1, wherein the dsDNA fragments are cell-free DNA (cfDNA) fragments.

4. The method according to claim 1, wherein a dsDNA fragment is modified prior to ligation of the double-stranded DNA adapters and wherein the modification comprises end-repairing, A-tailing, phosphorylation, or any combination thereof.

5. The method according to claim 1, wherein the test sample comprises whole blood, a blood fraction, plasma, serum, urine, fecal matter, saliva, a tissue biopsy, pleural fluid, pericardial fluid, cerebrospinal fluid, peritoneal fluid, or any combination thereof.

6. The method according to claim 1, wherein the test sample is a plasma sample.

7. The method according to claim 1, wherein the test sample comprises dsDNA fragments originating from healthy cells and from cancer cells.

8. The method according to claim 1, wherein the dsDNA adapters are ligated to a first end and a second end of the dsDNA fragments.

9. The method according to claim 1, wherein the dsDNA adapter comprises a fork-shaped sequencing adapter formed by annealing a pair of partially complementary oligonucleotides to one another, wherein the fork-shaped sequencing adapter comprises a first double-stranded region, formed from hybridization between the complementary regions, and a second single-stranded region.

10. The method according to claim 9, wherein the one or more modified bases are located at the 3' end of the double-stranded region of the fork-shaped sequencing adapter.

11. The method according to claim 9, wherein the one or more modified bases are located upstream of a 3' end of the fork-shaped sequencing adapter.

12. The method according to claim 1, wherein the dsDNA adapters are hairpin adapters or linear adapters.

13. The method according to claim 1, wherein the ligase is a T4 DNA ligase or a T7 DNA ligase.

14. The method according to claim 2, further comprising enriching the sequencing library for one or more target dsDNA fragments that are known to be, or suspected of being, indicative of cancer.

15. The method according to claim 2, wherein the sequence reads are obtained from a next-generation sequencing (NGS) procedure, massively parallel sequencing using a sequencing-by-synthesis procedure, or a paired-end sequencing procedure.

* * * * *

UNITED STATES PATENT AND TRADEMARK OFFICE
CERTIFICATE OF CORRECTION

PATENT NO. : 11,274,344 B2
APPLICATION NO. : 15/942214
DATED : March 15, 2022
INVENTOR(S) : Craig Betts and Byoungsok Jung It is certified that error appears in the above-identified patent and that said Letters Patent is hereby corrected as shown below:

On the Title Page

Item (71), Correct Applicant Name to read as GRAIL, LLC, Menlo Park, CA

Signed and Sealed this
Fifteenth Day of August, 2023

Katherine Kelly Vidal
*Director of the United States Patent and Trademark Office*